United States Patent
Prezewowsky

(10) Patent No.: US 11,641,157 B2
(45) Date of Patent: May 2, 2023

(54) MEDICAL DEVICE WITH FAIL-SAFE POWER SUPPLY

(71) Applicant: OLYMPUS WINTER & IBE GMBH, Hamburg (DE)

(72) Inventor: Thomas Prezewowsky, Teltow (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 21 days.

(21) Appl. No.: 17/206,687

(22) Filed: Mar. 19, 2021

(65) Prior Publication Data
US 2021/0296980 A1    Sep. 23, 2021

(30) Foreign Application Priority Data
Mar. 19, 2020 (DE) .................. 102020107614.2

(51) Int. Cl.
*H02M 1/32* (2007.01)

(52) U.S. Cl.
CPC ............. *H02M 1/322* (2021.05); *H02M 1/32* (2013.01)

(58) Field of Classification Search
CPC ......... H02M 1/322; H02M 1/32; H02M 7/003
See application file for complete search history.

(56) References Cited

U.S. PATENT DOCUMENTS

| | | | |
|---|---|---|---|
| 5,523,665 A | 6/1996 | Deaver | |
| 6,703,793 B2 | 3/2004 | Kitano | |
| 2003/0021134 A1* | 1/2003 | Elferich | H02M 1/4208 363/125 |
| 2011/0122668 A1* | 5/2011 | Lo | H02J 9/061 363/126 |

(Continued)

FOREIGN PATENT DOCUMENTS

| | | |
|---|---|---|
| DE | 10 2009 037 693 A1 | 3/2011 |
| JP | 2002-048375 A | 2/2002 |

(Continued)

OTHER PUBLICATIONS

Oct. 21, 2020 Office Action issued in German Patent Application No. 10 2020 107 614.2.

(Continued)

*Primary Examiner* — Adolf D Berhane
*Assistant Examiner* — Afework S Demisse
(74) *Attorney, Agent, or Firm* — Oliff PLC

(57) ABSTRACT

A medical device with a power supply for connecting to an AC power grid in the range of >50 $V_{AC}$ to 264 $V_{AC}$ (wide range) features a circuit for only connecting at least one discharge resistor in parallel to at least one smoothing capacitor if no AC input voltage is present at the power supply. The power supply features a rectifier and at least one smoothing capacitor for smoothing a direct voltage to be supplied by the power supply, as well as at least one discharge resistor for discharging the smoothing capacitor. The power supply features a circuit electrically connected to the discharge resistor and the smoothing capacitor, designed to detect a switched-on state of the medical device with an AC input voltage present at its power supply, and to only connect the discharge resistor in parallel to the smoothing capacitor if the circuit does not detect a switched-on state.

11 Claims, 3 Drawing Sheets

(56) References Cited

U.S. PATENT DOCUMENTS

Figure 1:
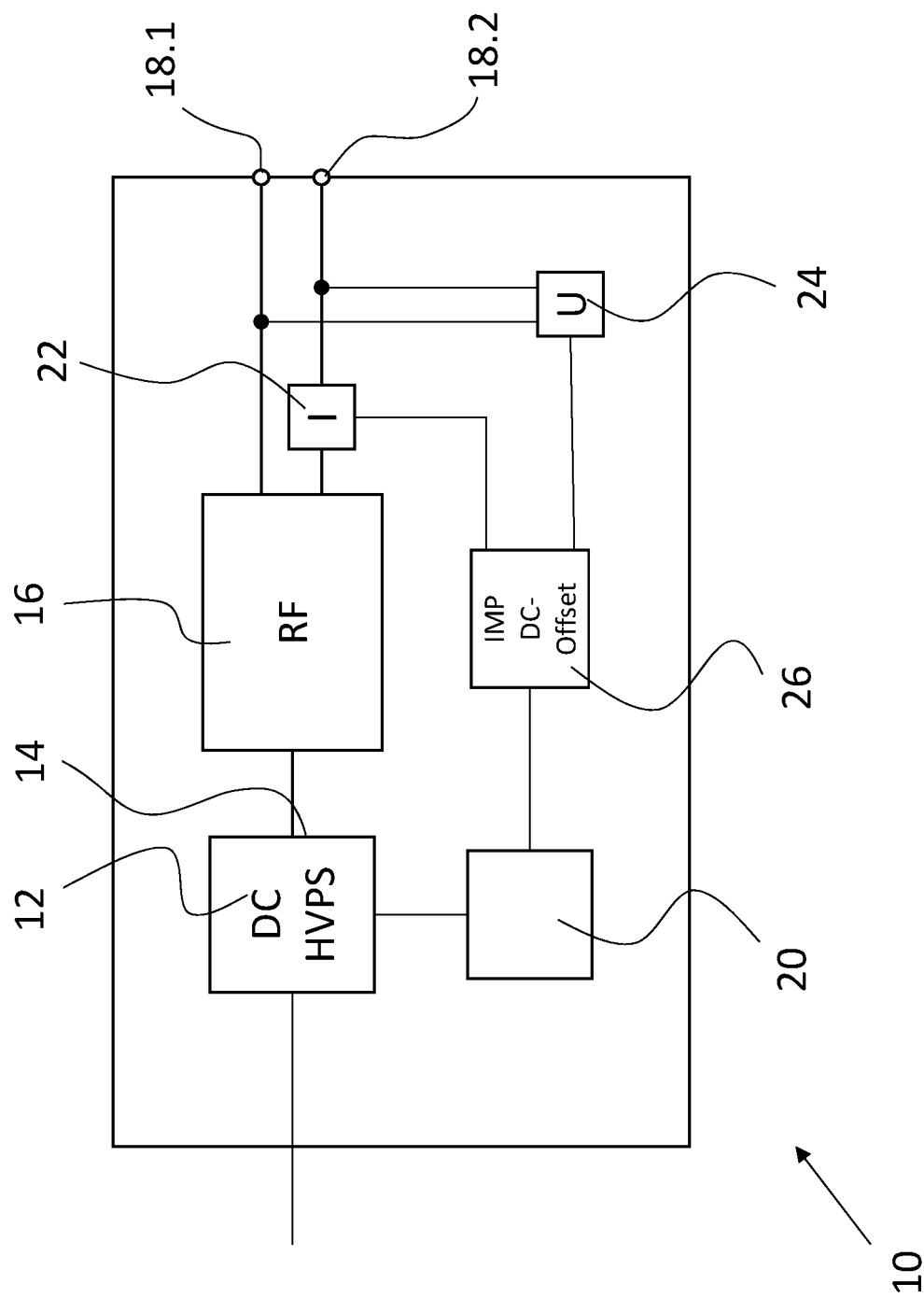

2012/0053578 A1   3/2012   Schall et al.

FOREIGN PATENT DOCUMENTS

| JP | 2002048375 A | * | 2/2002 |
| JP | 2002-262573 A | | 9/2002 |
| JP | 2002262573 A | * | 9/2002 |
| JP | 2006-204028 A | | 8/2006 |
| JP | 2006204028 A | * | 8/2006 |
| JP | 2007-207585 A | | 8/2007 |
| JP | 2007207585 A | * | 8/2007 |
| JP | 2008-011644 A | | 1/2008 |
| JP | 2011-234481 A | | 11/2011 |
| JP | 2011234481 A | * | 11/2011 |

OTHER PUBLICATIONS

Mar. 28, 2022, Office Action and Search Report issued in Japanese Patent Application No. 2021-044829.

* cited by examiner

MEDICAL DEVICE WITH FAIL-SAFE POWER SUPPLY

The invention relates to a medical device with a power supply for connecting to an AC power grid, wherein the power supply comprises a rectifier and at least one smoothing capacitor for smoothing the DC voltage to be supplied by the power supply, and at least one discharge resistor for discharging the smoothing capacitor. The invention relates in particular to an electrosurgical generator with outputs to which an electrosurgical instrument can be connected and at which a connected electrosurgical instrument can be provided with a high-frequency AC output voltage.

For safety reasons, capacitors of an electrical device should not hold any higher residual voltage a reasonable time after the capacitors have been shut off. This also applies to medical devices and in particular to high-voltage DC power supplies of electrosurgical generators. For this purpose, discharge resistors are provided that are located parallel to, and discharge, capacitors with high capacity.

U.S. Pat. No. 5,523,665 A discloses a power supply with a bridge rectifier and smoothing capacitors that are discharged via a resistor after the mains voltage is cut off.

The invention is based on the object of creating an improved power supply, in particular for a medical device like an electrosurgical generator, that fulfills the safety requirements.

According to the invention, this object is achieved with a medical device having a power supply for connecting to an AC power grid and comprising at least one circuit in order to only switch at least one discharge resistor parallel to at least one smoothing capacitor if no AC input voltage is present at the power supply.

The power supply features a rectifier and at least one smoothing capacitor for smoothing the DC voltage to be supplied by the power supply, and at least one discharge resistor for discharging the smoothing capacitor. The power supply further comprises a circuit that is electrically connected to the discharge resistor and the smoothing capacitor, and that is designed to detect a switched-on state of the medical device that carries an AC input voltage at its power supply, and to connect the discharge resistor in parallel to the smoothing capacitor only if no switched-on state is detected for the medical device.

The circuit features a first transistor (T2) for connecting the discharge resistor (R4, R5, R6, R7, R8, R9) in parallel to the smoothing capacitor (C1). The first transistor (T2) is arranged and dimensioned in such a way that it connects and causes the smoothing capacitor (C1) to discharge if a capacitor (C4), that is connected to the base or the gate of the first transistor (T2) and serves as a control capacitor, is sufficiently charged. The capacitor (C4) is discharged regularly by means of a second transistor (T1), which serves as a control transistor, as long as the mains voltage is fed to the power supply.

It is thus possible to securely detect the AC input voltage across the entire input voltage range of the medical device, and the additionally required power to feed into the detection circuit is minimized.

The circuit preferably features a switch for connecting the discharge resistor in parallel to the smoothing capacitor. The switch is preferably a field effect transistor.

The invention thus proposes a power supply with an electronic circuit that will only connect one or several discharge resistors in parallel to one or several corresponding capacitors of the power supply—in particular, smoothing capacitors—if the medical device is switched off. To this end, the supply voltage (AC voltage) is detected and used as the control factor.

The invention considers the findings that, depending on the voltage rating and capacity of the smoothing capacitors, lower or higher currents flow through these discharge resistors that generate a permanent power dissipation when switched on, thereby considerably increasing the current draw of e. g. an electrosurgical generator in standby mode. This raises the interior temperature of the medical device and reduces the mean operating time between failures of the medical device.

The rectifier preferably has a bridge rectifier, and the circuit is preferably configured to pick up a voltage between a connection on the input side of the bridge rectifier and a connection on the output side of the bridge rectifier, and to detect a mains voltage present at the connection on the input side of the bridge rectifier.

To this end, the circuit preferably features a voltage divider installed between an input of the bridge rectifier and the negative output of the bridge rectifier, and a first capacitor connected in parallel to a resistor of the voltage divider that filters interference pulses potentially occurring on the mains supply side when a mains voltage is present, and that ensures the necessary division ratio of the voltage divider.

Furthermore, the base-emitter path of the control resistor is preferably connected in parallel to the resistor of the voltage divider, and the control transistor connects in phase with the AC input voltage if a mains supply voltage in the range of >50 $V_{AC}$ . . . 264 $V_{AC}$ is present. The control transistor is thus preferably operated in an emitter circuit. The control transistor is preferably a bipolar junction transistor, in particular an NPN transistor. However, the control transistor can also be a PNP transistor, and the circuit can be respectively set up to be complementary. As an alternative, a corresponding circuit with a field effect transistor is also possible.

Preferably, a second capacitor is connected in parallel to a gate-drain path of the field effect transistor serving as a switch. This second capacitor, when charged, causes the field effect transistor to connect so that the at least one discharge resistor is connected in parallel to the at least one smoothing capacitor. The second capacitor is charged from the smoothing capacitor if there is no mains supply voltage present at the rectifier or its bridge rectifier, causing the field effect transistor that serves as a switch to connect, so that the at least one discharge resistor is connected in parallel to the at least one smoothing capacitor. This way the smoothing capacitor is discharged via the discharge resistor if there is no mains supply voltage present at an input of the rectifier.

The second capacitor is preferably connected in parallel to a collector-emitter path of the control transistor so that the second capacitor is discharged when the control transistor is connected. If the second capacitor is discharged, the field effect transistor serving as a switch blocks, so that the at least one discharge resistor is disconnected from the at least one smoothing capacitor. The control transistor connects if a mains supply voltage is present at the input of the rectifier, thereby causing the discharge resistor to be disconnected from the smoothing capacitor if a mains supply voltage is present.

The circuit preferably has one or several Zener diodes for voltage limitation. A respective Zener diode is provided in particular to protect the corresponding transistor.

The circuit preferably features several discharge resistors that are connected in parallel so as to also facilitate greater power dissipation when discharging the smoothing capacitor.

The at least one discharge resistor preferably has a resistance value between 47 kΩ and 120 kΩ. As a general rule, the resistance value of the discharge resistor should preferably be chosen such that 60 seconds after switching off the maximum AC input voltage, the DC voltage at the at least one smoothing capacitor has been reduced to less than 60 V. The preferred resistance value of the at least one discharge resistor thus results from the maximum AC input voltage and the capacity of the at least one smoothing capacitor.

The invention will now be explained in more detail using an embodiment and referencing the figures. The figures show the following:

FIG. 1: shows a schematic diagram of several components of an electrosurgical generator for supplying a high-frequency AC voltage to an electrosurgical instrument.

Figure 2:
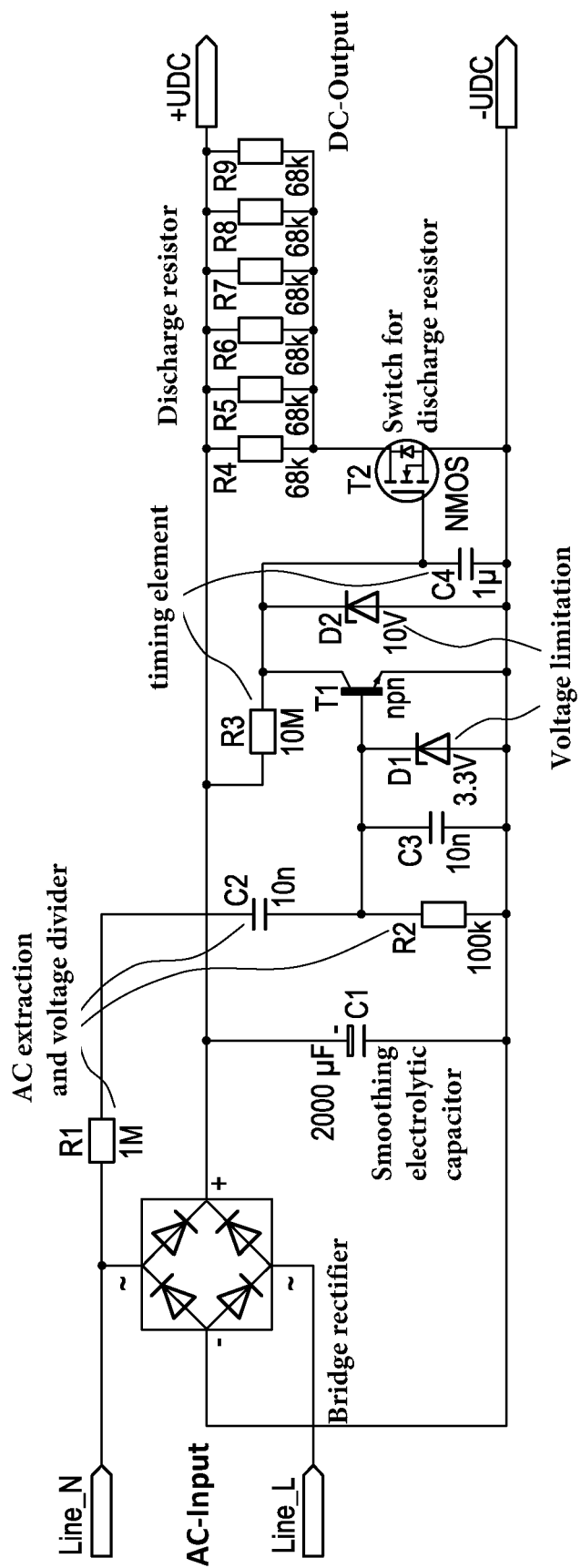

FIG. 2: shows a circuit that enables a connection in parallel according to the invention of at least one discharge resistor to at least one smoothing capacitor of a DC power supply after it has been disconnected from a mains supply AC voltage.

Figure 3:
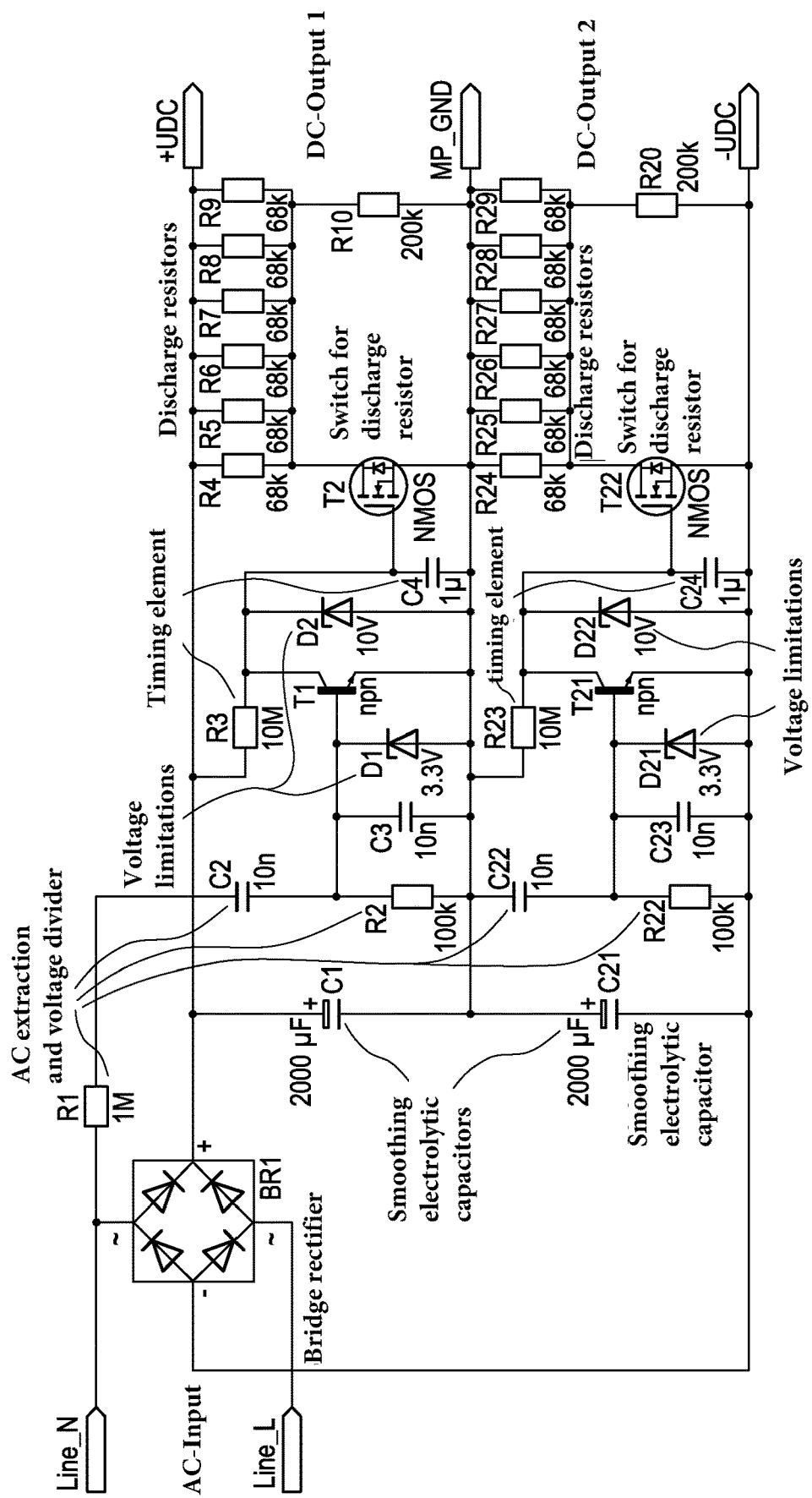

FIG. 3 shows a circuit that is similar to the circuit depicted in FIG. 2, but for a power supply that provides a symmetrical output voltage.

FIG. 1 shows a medical device using the example of an electrosurgical generator 10. As can be seen in FIG. 1, the electrosurgical generator 10 has a high-voltage power supply 12 (HVPS) for this purpose that can be connected to the public power grid, for example, and provides a high-voltage direct current at its output 14. This high-voltage direct current is fed into a high-frequency part 16 of the electrosurgical generator 10. The high-frequency part 16 of the electrosurgical generator 10 serves as an inverter and generates a high-frequency alternating voltage that is supplied via an output transformer (not shown) of the high-frequency part 16 to the outputs 18.1 and 18.2 of the electrosurgical generator 10. An electrosurgical instrument can be connected to the outputs 18.1 and 18.2 of the electrosurgical generator 10. The output power of the electrosurgical generator 10 can be controlled or adjusted via a control unit 20 and the measuring units 22 and 24 as well as an evaluation unit 26 for deriving values such as impedance, etc. from measured values.

Current high-frequency electrosurgical generators generate the high-frequency output voltage in two steps. Initially, the mains input voltage is converted into a variable direct voltage. This DC voltage serves as the input voltage for an inverter circuit of the high-voltage power supply 12 whose output voltage increases proportionally to the input voltage. The output voltage (and thereby also the current and power) can thus be controlled using the input voltage.

Regarding the high-voltage power supply 12, the rule applies that—according to IEC 60601-1, as amended—it is necessary to take precautions that energy storage devices (mostly capacitors) carry a voltage of <60 V one minute after the electronic medical device has been shut off.

FIG. 2 shows an example of a high-voltage power supply according to the invention.

It features an electronic circuit that only connects the required discharge resistors in parallel to the corresponding capacitors when the medical device is switched off. To this end, the supply voltage (AC voltage) is detected and used as a control factor. The prerequisite for this is that the device is operated at a supply voltage between 100 and 240 VAC.

A power supply for generating a DC output voltage from an AC input voltage typically features a bridge rectifier made up of four diodes for rectification of the alternating current, and one or several smoothing capacitors for smoothing the DC output voltage. The bridge rectifier features two inputs for the AC input voltage and two outputs for the DC output voltage. One output has a positive terminal, and the other output of the bridge rectifier has a negative terminal.

After the supply voltage—i. e. the AC input current—has been shut off, the smoothing capacitors are still charged. The exemplary embodiment in FIG. 2 shows a smoothing capacitor C1 in the form of an electrolytic capacitor with a capacity of 2000 μF. Instead of a single smoothing capacitor, it is also possible to provide several smoothing capacitors that are connected in parallel or in series. If, for example, the DC output voltage of the high-voltage power supply is 300 V, the smoothing capacitors can be connected in series in pairs so that each smoothing capacitor only reduces a maximum voltage of 150 V. The smoothing capacity can be increased by connecting the smoothing capacitors in parallel.

According to the exemplary embodiment in FIG. 2, a total of 6 discharge resistors R4 through R9 are provided; they are connected in parallel so as to have a higher load capacity collectively. Each of the resistors R4 through R9 has a resistance value of 68 kΩ.

In order to discharge the smoothing capacitor C1 after the supply voltage has been shut off, the 6 discharge resistors R4 through R9 are connected in parallel to the smoothing capacitor C1. Generally, the number and dimensioning of the discharge resistors are preferably chosen in relation to the capacity of the smoothing capacitors and the maximum voltage such that the discharge resistors allow for a discharge capacity that is necessary for reducing the maximum voltage at the capacitors to under 60 V in no more than 60 seconds.

All 6 discharge resistors R4 through R9 are disconnected from the smoothing capacitor C1 when the medical device is in operation, so that they do not permanently discharge power when the medical device is in operation. A field effect transistor T2, which serves as a switch, is used for this purpose.

The field effect transistor T2 is controlled by a detection circuit that is designed to detect the presence of an AC input voltage, and to only connect the field effect transistor—thereby connecting the 6 discharge resistors R4 through R9 in parallel to the smoothing capacitor C1—if no AC input voltage is detected at the power supply of the medical device.

For detecting the supply voltage and for driving the field effect transistor T2, the detection circuit has the resistors R1 (1 MΩ) and R2 (100 kΩ) as well as a capacitor C2 (10 nF) that are connected in series between an input of the bridge rectifier and the negative output of the bridge rectifier.

The resistors R1 (1 MΩ) and R2 (100 kΩ), together with the capacitor C2 (10 nF), form a voltage divider. A capacitor C3 (10 nF) is connected in parallel to the resistor R2. The voltage is picked up between the capacitor C2 and the resistor R2 and supplied to the base of an NPN transistor T1. The transistor T1 is thus a bipolar transistor that is operated in an emitter circuit and serves as a control transistor that, when connected, causes the capacitor C4 to discharge. The capacitor C4 is connected in parallel to the smoothing capacitor C1, and charged by the smoothing capacitor C1 via a resistor R3 that is connected in series to the capacitor C4 if the transistor T1 is not connected.

The AC voltage is uncoupled prior to rectification via the resistor R1 and the capacitor C2, and the resistor R2 and capacitor C3 filter and reduce the AC voltage such that it can be processed by the transistor T1 (an NPN transistor). As long as AC voltage is present, the transistor T1 is connected in phase with the AC voltage, thereby preventing that the capacitor C4 can be charged via the resistor R3. This causes the transistor T2 to remain blocked, and the discharge resistors are currentless.

Two Zener diodes D1 (3.3 V) and D2 (10 V) each cause a voltage limitation. The Zener diode D1 is connected in parallel to the resistor R2, the capacitor C3, and the base-emitter path of the transistor T1. The Zener diode D2 and a capacitor C4 (1 µF) are connected in parallel to the collector-emitter path of the transistor T1. As long as the transistor T1 is connected, the voltage does not decrease via the capacitor C4 so that it is not charged. When the transistor T1 blocks, the capacitor is charged via the resistor R3. For this purpose, the resistor R3 and the capacitor C4 are connected in series between the two outputs of the bridge rectifier and parallel to the smoothing capacitor C1. The resistor R3 determines how fast the capacitor C4 is charged and thus serves as a timing element. The Zener diode D2 limits the voltage via the capacitor C4 to a maximum of 10 volts. The capacitor C4 can thus be charged to a maximum of 10 volts.

The gate of the field effect transistor T2 is controlled by the voltage via the capacitor C4.

If the AC voltage at the input of the bridge rectifier is switched off, the transistor T1 blocks, and the capacitor C4 (1 µF) can be charged up to 10 V via the resistor R3. This renders the field effect transistor T2 conductive, and the discharge resistors R4 through R9 discharge the smoothing capacitor C1. When the AC voltage returns, the capacitor C4 is discharged via the transistor T1, and the field effect transistor T2 blocks. This renders the discharge resistors R4 through R9 currentless again.

FIG. 3 shows a circuit of a power supply for generating a symmetrical DC output voltage. The circuit is, for the most part, a doubling of the circuit shown in FIG. 2. The two additional resistors R10 and R20 are used to balance the DC voltage at the smoothing electrolytic capacitors. If the DC voltage between the positive DC output voltage +UDC and the negative DC output voltage −UDC is not loaded against ground MP_GND, different levels of leakage currents in the capacitors could cause unbalanced high voltages against ground MP_GND to form when the AC supply voltage is present and the discharge resistors are not switched on. R10 and R20 are preferably dimensioned in such a way that they hold approximately five times the leakage current of the capacitors.

The circuit is designed for a supply voltage (AC voltage at the input of the bridge rectifier) between 100 and 240 VAC.

The invention claimed is:

1. A medical device comprising:
   a power supply for connecting to an AC power grid, the power supply having:
      a bridge rectifier;
      a smoothing capacitor for smoothing a DC voltage to be supplied by the power supply;
      a discharge resistor for discharging the smoothing capacitor; and
      a circuit that is electrically connected to the discharge resistor and the smoothing capacitor and configured to detect a switched-on state of the medical device, with an AC input voltage present at its power supply, across an entire input voltage range, and to only connect the discharge resistor in parallel to the smoothing capacitor if the circuit does not detect a switched-on state of the medical device, the circuit having:
      a first transistor for connecting the discharge resistor in parallel to the smoothing capacitor that is arranged and dimensioned to connect and cause the smoothing capacitor to discharge if a control capacitor connected to a base or a gate of the first transistor is sufficiently charged, the control capacitor being connected to a control transistor that is arranged and dimensioned to regularly connect and discharge the control capacitor as long as the power supply receives a mains voltage;
      a first resistor;
      a second resistor; and
      a circuit capacitor, the first resistor, the second resistor, and the circuit capacitor being connected in series between an input of the bridge rectifier and a negative output of the bridge rectifier, a junction between the second resistor and the circuit capacitor being connected to a base of the control transistor.

2. The medical device according to claim 1, wherein the first transistor is a field effect transistor.

3. The medical device according to claim 2, further comprising:
   a second capacitor connected in parallel to a gate-drain path of the field effect transistor, the second capacitor, when charged, causing the field effect transistor to connect so that the discharge resistor is connected in parallel to the smoothing capacitor.

4. The medical device according to claim 1, wherein the circuit is configured to pick up a voltage between a connection on an input side of the bridge rectifier and a connection on an output side of the bridge rectifier and to detect a presence of the mains voltage present at the connection on the input side of the bridge rectifier.

5. The medical device according to claim 4, wherein the circuit has a voltage divider comprised of the first resistor, the second resistor, and the circuit capacitor, and a first capacitor that is connected in parallel to the second resistor and charged to a voltage defined by the voltage divider if the mains voltage is present.

6. The medical device according to claim 1, wherein a base-emitter path of the control transistor is connected in parallel to the second resistor, and the control transistor connects if the mains voltage is present in a range of >50 $V_{AC}$ ... 264 $V_{AC}$ is present.

7. The medical device according to claim 1, wherein the control transistor is a bipolar transistor.

8. The medical device according to claim 7, wherein the second capacitor is connected in parallel to a collector-emitter path of the control transistor so that the second capacitor is discharged when the control transistor is connected, so that the discharge resistor is disconnected from the smoothing capacitor if the mains voltage is present at the input of the bridge rectifier.

9. The medical device according to claim 1, wherein the circuit has a Zener diode for voltage limitation.

10. The medical device according to claim 1, further comprising several of the discharge resistors connected in parallel.

11. The medical device according to claim 1, wherein the discharge resistor has a resistance value between 47 kΩ and 120 kΩ.

* * * * *